US012647764B2

(12) United States Patent
Gustavson et al.

(10) Patent No.: US 12,647,764 B2
(45) Date of Patent: *Jun. 2, 2026

(54) DETAILED ALARM MESSAGES AND SUPPORT

(71) Applicant: WEST AFFUM HOLDINGS DAC, Dublin (IE)

(72) Inventors: Laura M. Gustavson, Redmond, WA (US); David P. Finch, Bothell, WA (US); Steven E. Sjoquist, Lynwood, WA (US); Heather Mareth, Kirkland, WA (US); Erik L. Schneider, Kirkland, WA (US); Zoie R. Engman, Kirkland, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/625,122

(22) Filed: Apr. 2, 2024

(65) Prior Publication Data

US 2024/0267720 A1 Aug. 8, 2024

Related U.S. Application Data

(63) Continuation of application No. 17/322,754, filed on May 17, 2021, now Pat. No. 11,950,174.
(Continued)

(51) Int. Cl.
*H04W 4/90* (2018.01)
*A61N 1/39* (2006.01)
(Continued)

(52) U.S. Cl.
CPC ............ *H04W 4/90* (2018.02); *A61N 1/3904* (2017.08); *A61N 1/3993* (2013.01); *G16H 10/60* (2018.01); *H04L 67/55* (2022.05); *H04W 4/12* (2013.01)

(58) Field of Classification Search
CPC .................................................. A61B 5/02438
See application file for complete search history.

(56) References Cited

U.S. PATENT DOCUMENTS

| | | | |
|---|---|---|---|
| 3,724,355 A | 4/1973 | Busch et al. | |
| 3,724,455 A | 4/1973 | Unger | |
| | (Continued) | | |

FOREIGN PATENT DOCUMENTS

| | | |
|---|---|---|
| DE | 102005060985 A1 | 6/2007 |
| EP | 2305110 A1 | 4/2011 |
| | (Continued) | |

OTHER PUBLICATIONS

HeartStart MRx and XL AED Algorithm—Application Note, Jul. 2011, Edition 2 Philips Healthcare, USA.
(Continued)

*Primary Examiner* — Fabricio R Murillo Garcia
(74) *Attorney, Agent, or Firm* — Seed Intellectual Property Law Group LLP

(57) ABSTRACT

In one embodiment, a method of alerting a user of a WCD is described. The method includes receiving an alert from the WCD on a remote device associated with the user and in communication with the WCD and transcribing the alert into a message for the user. The method also includes personalizing the message for the user and delivering the message to the user via the remote device.

20 Claims, 8 Drawing Sheets

Related U.S. Application Data

(60) Provisional application No. 63/120,712, filed on Dec. 2, 2020.

(51) Int. Cl.

| | |
|---|---|
| *G16H 10/60* | (2018.01) |
| *H04L 67/55* | (2022.01) |
| *H04W 4/12* | (2009.01) |

(56) References Cited

U.S. PATENT DOCUMENTS

| | | | |
|---|---|---|---|
| 4,583,524 | A | 4/1986 | Hutchins |
| 4,619,265 | A | 10/1986 | Morgan et al. |
| 4,666,432 | A | 5/1987 | McNeish et al. |
| 4,698,848 | A | 10/1987 | Buckley |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Bornn et al. |
| 5,353,793 | A | 10/1994 | Bornn |
| RE34,800 | E | 11/1994 | Hutchins |
| 5,394,892 | A | 3/1995 | Kenny et al. |
| 5,405,362 | A | 4/1995 | Kramer et al. |
| 5,429,593 | A | 7/1995 | Matory |
| 5,474,574 | A | 12/1995 | Payne et al. |
| 5,618,208 | A | 4/1997 | Crouse et al. |
| 5,662,690 | A | 9/1997 | Cole et al. |
| 5,708,978 | A | 1/1998 | Johnsrud |
| 5,741,306 | A | 4/1998 | Glegyak et al. |
| 5,782,878 | A | 7/1998 | Morgan et al. |
| 5,792,204 | A | 8/1998 | Snell |
| 5,902,249 | A | 5/1999 | Lyster |
| 5,913,685 | A | 6/1999 | Hutchins |
| 5,944,669 | A | 8/1999 | Kaib |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,263,238 | B1 | 7/2001 | Brewer et al. |
| 6,280,461 | B1 | 8/2001 | Glegyak et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder et al. |
| 6,427,083 | B1 | 7/2002 | Owen et al. |
| 6,437,083 | B1 | 8/2002 | Brack et al. |
| 6,450,942 | B1 | 9/2002 | Lapanashvili et al. |
| 6,529,875 | B1 | 3/2003 | Nakajima et al. |
| 6,546,285 | B1 | 4/2003 | Owen et al. |
| 6,671,545 | B2 | 12/2003 | Fincke |
| 6,681,003 | B2 | 1/2004 | Linder et al. |
| 6,762,917 | B1 | 7/2004 | Verbiest et al. |
| 7,065,401 | B2 | 6/2006 | Worden |
| 7,099,715 | B2 | 8/2006 | Korzinov et al. |
| 7,212,850 | B2 | 5/2007 | Prystowsky et al. |
| 7,559,902 | B2 | 7/2009 | Ting et al. |
| 7,587,237 | B2 | 9/2009 | Korzinov et al. |
| 7,753,759 | B2 | 7/2010 | Pintor et al. |
| 7,865,238 | B2 | 1/2011 | Brink |
| 7,870,761 | B2 | 1/2011 | Valentine et al. |
| 7,907,996 | B2 | 3/2011 | Prystowsky et al. |
| 7,941,207 | B2 | 5/2011 | Korzinov |
| 7,974,689 | B2 | 7/2011 | Volpe et al. |
| 8,135,462 | B2 | 3/2012 | Owen et al. |
| 8,140,154 | B2 | 3/2012 | Donnelly et al. |
| 8,369,944 | B2 | 2/2013 | Macho et al. |
| 8,527,028 | B2 | 9/2013 | Kurzweil et al. |
| 8,548,557 | B2 | 10/2013 | Garstka et al. |
| 8,560,044 | B2 | 10/2013 | Kurzweil et al. |
| 8,615,295 | B2 | 12/2013 | Savage et al. |
| 8,644,925 | B2 | 2/2014 | Volpe et al. |
| 8,676,313 | B2 | 3/2014 | Volpe et al. |
| 8,706,255 | B2 | 4/2014 | Phillips et al. |
| 8,742,349 | B2 | 6/2014 | Urbon et al. |
| 8,897,860 | B2 | 11/2014 | Volpe et al. |
| 8,904,214 | B2 | 12/2014 | Volpe et al. |
| 8,965,500 | B2 | 2/2015 | Macho et al. |
| 9,008,801 | B2 | 4/2015 | Kaib et al. |
| 9,084,583 | B2 | 7/2015 | Mazar et al. |
| 9,089,685 | B2 | 7/2015 | Sullivan et al. |
| 9,119,547 | B2 | 9/2015 | Cazares et al. |
| 9,131,901 | B2 | 9/2015 | Volpe et al. |
| 9,132,267 | B2 | 9/2015 | Kaib |
| 9,265,432 | B2 | 2/2016 | Warren et al. |
| 9,345,898 | B2 | 5/2016 | Piha et al. |
| 9,408,548 | B2 | 8/2016 | Volpe et al. |
| 9,445,719 | B2 | 9/2016 | Libbus et al. |
| 9,454,219 | B2 | 9/2016 | Volpe et al. |
| 9,579,020 | B2 | 2/2017 | Libbus et al. |
| 9,592,403 | B2 | 3/2017 | Sullivan |
| 9,598,799 | B2 | 3/2017 | Shoshani et al. |
| 9,675,804 | B2 | 6/2017 | Whiting et al. |
| 9,724,008 | B2 | 8/2017 | Sullivan et al. |
| 9,878,171 | B2 | 1/2018 | Kaib |
| 9,895,105 | B2 | 2/2018 | Romem |
| 9,901,741 | B2 | 2/2018 | Chapman et al. |
| RE46,926 | E | 7/2018 | Bly et al. |
| 10,016,613 | B2 | 7/2018 | Kavounas |
| 10,076,656 | B2 | 9/2018 | Dar et al. |
| 10,192,387 | B2 | 1/2019 | Brinig et al. |
| 10,307,133 | B2 | 6/2019 | Kaib |
| 10,463,867 | B2 | 11/2019 | Kaib et al. |
| 10,589,110 | B2 | 3/2020 | Oskin et al. |
| 10,599,814 | B2 | 3/2020 | Landrum et al. |
| 2002/0078204 | A1* | 6/2002 | Newell ............... G06F 21/6245 709/225 |
| 2002/0181680 | A1 | 12/2002 | Linder et al. |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2006/0004680 | A1* | 1/2006 | Robarts ................... G06F 16/40 706/46 |
| 2006/0173499 | A1 | 8/2006 | Hampton et al. |
| 2008/0312709 | A1 | 12/2008 | Volpe et al. |
| 2009/0005827 | A1 | 1/2009 | Weintraub et al. |
| 2010/0007413 | A1 | 1/2010 | Herleikson |
| 2010/0298899 | A1 | 11/2010 | Donnelly et al. |
| 2011/0022105 | A9 | 1/2011 | Owen et al. |
| 2011/0288604 | A1 | 11/2011 | Kaib et al. |
| 2011/0288605 | A1 | 11/2011 | Kaib et al. |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0191476 | A1 | 7/2012 | Reid et al. |
| 2012/0265265 | A1 | 10/2012 | Razavi et al. |
| 2012/0283794 | A1 | 11/2012 | Kaib et al. |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2013/0085538 | A1 | 4/2013 | Volpe et al. |
| 2013/0144355 | A1 | 6/2013 | Macho et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0012144 | A1 | 1/2014 | Crone |
| 2014/0025131 | A1 | 1/2014 | Sullivan |
| 2014/0046391 | A1 | 2/2014 | Cowan et al. |
| 2014/0070957 | A1 | 3/2014 | Longinotti-Buitoni et al. |
| 2014/0163663 | A1 | 6/2014 | Poddar et al. |
| 2014/0324112 | A1 | 10/2014 | Macho et al. |
| 2014/0378812 | A1 | 12/2014 | Saroka et al. |
| 2015/0039053 | A1 | 2/2015 | Kaib et al. |
| 2015/0109125 | A1* | 4/2015 | Kaib ..................... G08B 3/10 340/539.12 |
| 2015/0161554 | A1 | 6/2015 | Sweeney et al. |
| 2015/0297135 | A1 | 10/2015 | Shoshani et al. |
| 2015/0328472 | A1 | 11/2015 | Sullivan et al. |
| 2016/0004831 | A1 | 1/2016 | Carlson et al. |

(56)                References Cited

U.S. PATENT DOCUMENTS

| | | | |
|---|---|---|---|
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0256104 A1 | 9/2016 | Romem et al. | |
| 2016/0283900 A1 | 9/2016 | Johnson et al. | |
| 2016/0287172 A1* | 10/2016 | Morris | A61B 5/7264 |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0162840 A1 | 6/2017 | Pendry | |
| 2017/0319862 A1 | 11/2017 | Foshee, Jr. et al. | |
| 2017/0367591 A1 | 12/2017 | Jorgensen | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0242920 A1* | 8/2018 | Hresko | A61B 5/0006 |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0235936 A1 | 8/2019 | Murdock et al. | |
| 2019/0321650 A1 | 10/2019 | Raymond et al. | |
| 2020/0105404 A1* | 4/2020 | Major | G16H 40/20 |
| 2020/0108260 A1 | 4/2020 | Haddad et al. | |
| 2021/0361217 A1* | 11/2021 | Attia | A61B 5/349 |

FOREIGN PATENT DOCUMENTS

| | | | |
|---|---|---|---|
| JP | 4320257 | B2 | 8/2009 |
| JP | 2014526282 | A | 10/2014 |
| JP | 5963767 | B2 | 8/2016 |
| WO | 98/39061 | A2 | 9/1998 |
| WO | 2011/146448 | A1 | 11/2011 |
| WO | 2012/064604 | A1 | 5/2012 |
| WO | 2012/151160 | A1 | 11/2012 |
| WO | 2015/056262 | A1 | 4/2015 |

OTHER PUBLICATIONS

Helmut U. Klein et al., "Risk Stratification for Implantable Cardioverter Defibrillator Therapy: The Role of the Wearable Cardioverter-Defibrillator, Clinical update," European Heart Journal, European Society of Cardiology, May 31, 2013, pp. 1-14.

LIFECOR "LifeVest System Model WCD 3100 Operator's Manual", 2006, PN 20B0040 Rev FI, Zoll Lifecor Corporation, Pittsburgh, PA.

"LifeVest Model 4000 Patient Manual", Zoll, 2009, PN 20B0047 Rev B.

Pagan-Carlo et al., "Encircling Overlapping Multipulse Shock Waveforms for Transthoracic Defibrillation," JACC Journals, Dec. 1998, vol. 32, Issue 7, pp. 2065-2071.

"The LifeVest Network/Patient Data Management System", Zoll, 2015, 20C0498 Rev A.

Zoll, LifeVest, Proven protection from Sudden Cardiac Death, 2017, Pittsburgh PA, USA, 4 pages.

International Search Report and Written Opinion for PCT Application No. PCT/US2015/051726, dated May 20, 2016, European Patent Office, Rijswijk, (11 pages).

Non-Final Office Action for U.S. Appl. No. 17/322,754 dated Feb. 2, 2023 (64 Pages).

Final Office Action for U.S. Appl. No. 17/322,754 dated Jun. 23, 2023 (38 Pages).

Notice of Allowance for U.S. Appl. No. 17/322,754 dated Nov. 24, 2023 (41 Pages).

* cited by examiner

1000

Receive a message to troubleshoot a
problem with the WCD
1002

Prompt a patient to use the remote
device to troubleshoot a WCD issue
1004

Access a camera on the remote
device
1006

Use augmented reality to ascertain
and help the patient troubleshoot the
problem
1008

1100

Receive an emergency
alert from the WCD
1102

Activate emergency alert
protocol
1104

DETAILED ALARM MESSAGES AND SUPPORT

CROSS-REFERENCE TO RELATED PATENT APPLICATIONS

This patent application is a continuation patent application of U.S. patent application Ser. No. 17/322,754, filed May 17, 2021, now U.S. Pat. No. 11,950,174 which claims benefit of U.S. Provisional Patent Application No. 63/120,712 filed Dec. 2, 2020, both of which are incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death quickly, e.g., within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest and continuously monitors the patient's intracardiac electrogram (IEGM). If certain types of heart arrhythmias are detected, then the ICD delivers an electric shock through the heart.

As a further precaution, people who have been identified to have an increased risk of SCA may wear a Wearable Cardioverter Defibrillator (WCD) system until an ICD is implanted. Early versions of such systems were called wearable cardiac defibrillator systems. A WCD system typically includes a harness, vest, belt, or other garments that the patient wears. The WCD system further includes electronic components, such as a defibrillator and electrodes, coupled to the harness, vest, or another garment. When the patient wears the WCD system, the electrodes may electrically contact the patient's skin and aid in sensing the patient's electrocardiogram (ECG). If a shockable heart arrhythmia (e.g., ventricular fibrillation or VF) is detected from the ECG, then the defibrillator delivers an appropriate electric shock through the patient's body through the heart. The delivered shock may restart the patient's heart and save the patient's life.

BRIEF SUMMARY

This summary is provided to introduce a selection of concepts in a simplified form that is further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs and methods.

In one embodiment, a method to alert a user of a status or condition wearable cardioverter defibrillator (WCD) is described. The method includes determining when a condition requires user alert and pushing the patient alert to a remote device in communication with the WCD and associated with the user based at least in part on the determining.

In some embodiments, the method may include pushing user health and location data to the remote device. The data may include at least one of an age, weight, cardiac history, location of the user, or some combination thereof. In some embodiments, the method may include determining when the condition requires intervention and pushing an alert to the remote device based on the required intervention. In some embodiments, the method may include detecting a cardiac event requiring medical intervention and pushing an emergency alert to the remote device to activate an emergency protocol.

In one embodiment, a method of alerting a user of a WCD is described. The method includes receiving an alert from the WCD on a remote device associated with the user and in communication with the WCD and transcribing the alert into a message for the user. The method also includes personalizing the message for the user and delivering the message to the user via the remote device.

In some embodiments, delivering the message to the user may include delivering a unique message alert with a personalized message presentation. In some embodiments, the personalized message may include a name of the user. In some embodiments, the message may include one or more of an audio message, a voice message, and a video message.

In some embodiments, delivering the message to the user may include delivering a unique message alert with a personalized message presentation based at least in part on preferences selected by the user. Delivering the message to the user may include delivering a unique message alert with a personalized message presentation based at least in part on learned preferences based on user interactions.

In some embodiments, the method may include receiving an alert to troubleshoot a problem with the WCD and prompting the user to use the remote device to troubleshoot the problem with the WCD. The method may request permission to access a camera on the remote device and use the camera to troubleshoot the problem with the WCD when permission is granted.

In some embodiments, the method may include receiving an emergency alert from the WCD and activating an emergency alert protocol. The method may further include determining a location of the user and transmitting the location of the user to emergency personnel. The method may also include transmitting user data to the emergency personnel. In some embodiments, the method may contact an emergency contact per the emergency alert protocol. The method may also contact an attending physician of the user and deliver the emergency alert to the attending physician.

In some embodiments, the method may include tracking user interaction with the remote device and learning preferred user interaction based at least in part on the tracking. The method may also personalize alerts and notifications to the user based on the preferred user interaction. In some embodiments, the method may store the alert from the WCD in a memory of the remote device.

In one embodiment, a method of alerting a user of a WCD is described. The method includes receiving an alert from the WCD on a remote device associated with the user and transcribing the alert into a message on the remote device. The method also includes personalizing the message from the WCD into a unique message with a name of the user and delivering the unique message to the user via the remote device. Finally, the method stores the alert from the WCD in a memory of the remote device.

BRIEF DESCRIPTION OF THE DRAWINGS

The foregoing aspects and many of the attendant advantages of this disclosure will become more readily appreciated as the same becomes better understood by reference to the following detailed description, when taken in conjunction with the accompanying drawings, wherein.

DETAILED DESCRIPTION

Figure 1:
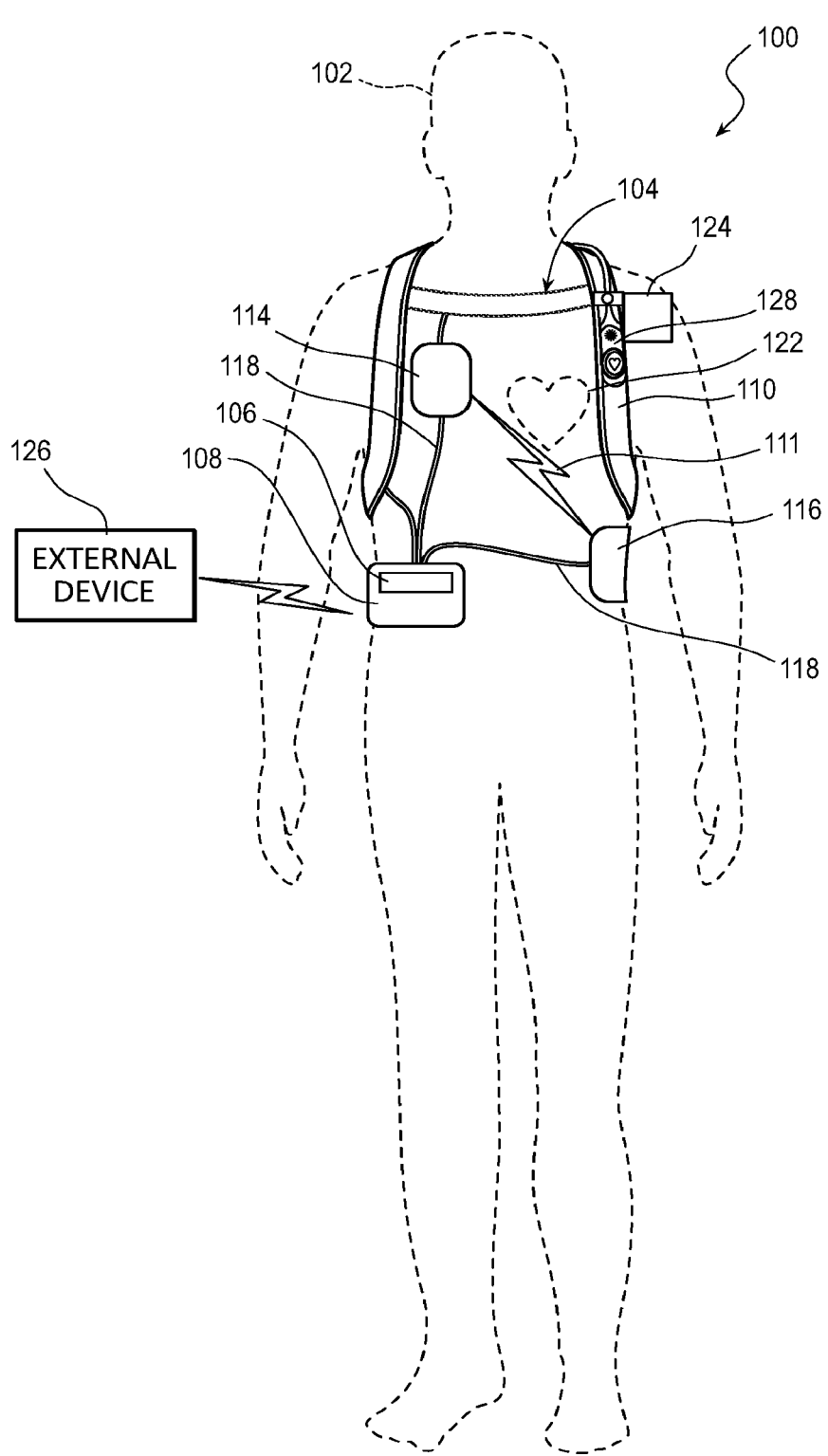
FIG. 1 is a diagram of a sample WCD system in accordance with exemplary embodiments described herein.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or limit the disclosure to the precise forms disclosed.

In the following description, specific details are set forth to provide a thorough understanding of exemplary embodiments of the present disclosure. However, it will be apparent to one skilled in the art that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest. The WCD system uses alarms to keep users informed of equipment and physiological conditions that may require the user's attention. However, the WCD itself may have precursory information. For example, the WCD system may communicate basic alarm content in which detailed alert information may be perfunctory or difficult to ascertain. The alert content may be available on the large defibrillator module, which does not allow the patient to interact with the device discretely. The alert content also uses memory, battery, and other resources of the defibrillator module.

By linking the WCD system to at least one remote device, the alert and alarm messages may become more meaningful and impactful to a patient and the patient's team. The term remote device and mobile device may be used interchangeably throughout the application. The patient may discretely receive and view information from the WCD device. However, all of the information is still maintained and controlled by the WCD. The WCD remains fully operational and effective without the mobile device application, thereby not compromising the patient's safety or health. The mobile application and remote device merely aid in the patient's comfort of interfacing with the WCD system.

In some embodiments, the mobile device may enhance the patient's interactions with the WCD unit. For example, the mobile device may present content in multiple formats, including videos, interactive animations, three-dimensional visualizations, among other methods. In some embodiments, the remote device may uniquely customize the alerts through the application. For example, the remote device may include a personalization such as the patient's name in its alerts. In some embodiments, the remote device may detect and utilize a patient's location when issuing alarms. For example, the remote device may detect when devices are present, which may interfere with the operation of the WCD.

In further embodiments, the patient may customize the messages. For example, some patients may prefer text messages or text alerts. Others may wish to receive a voice memo or a phone call to convey information. In some embodiments, patients may wish to receive one or more videos. The videos may contain an alert or information on troubleshooting a potential problem. If the remote device includes a camera, the remote device may use augmented reality to help a patient troubleshoot a potential issue with the WCD system.

In some embodiments, the remote device may also tailor the messages and alerts to increase patient response time. For example, the system may learn the preferred presentation of alarm message content and further customize future message appearances and delivery of the content. The system may track patient responses to specific messages to determine which messages are delivered and addressed efficiently and effectively. The delivery may include the type of messages, such as voice, text, or video, but may also include the alert mode programmed into the phone, the time of day, environmental concerns, and the like. The system may begin to tailor the message delivery to increase the responsivity of a patient.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT), or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102, such as in a cart, bag, stroller, wheelchair, or other vehicles.

The external defibrillator 108 may be coupled to the support structure 110 or carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in several ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso by being attached to the skin of patient 102, simply pressed against the skin directly or through garments, etc. In some embodiments, the electrodes 114, 116 are not necessarily pressed against the skin but become biased that way upon sensing a condition that could merit intervention by the WCD system 104. In addition, many of the components of defibrillator 108 can be considered coupled to support structure 110 directly or indirectly via at least one of the defibrillation electrodes 114, 116.

The WCD system 104 may defibrillate the patient 102 by delivering an electrical charge, pulse, or shock 111 to the patient 102 through a series of electrodes 114, 116 positioned on the torso. For example, when defibrillation electrodes 114, 116 are in good electrical contact with the torso of patient 102, the defibrillator 108 can administer, via electrodes 114, 116, a brief, strong electric pulse 111 through the body. The electric pulse 111 is also known as shock, defibrillation shock, therapy, electrotherapy, therapy shock, etc. The electric pulse 111 is intended to go through and restart heart 122 in an effort to save the life of patient 102. The electric pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124, which may also be known as an outside monitoring device. The monitoring device 124 may monitor at least one local parameter. Local parameters may include a physical state of the patient 102, such as ECG, movement, heart rate, pulse, temperature, and the like. Local parameters may also include a parameter of the WCD 104, environmental parameters, or the like. For example, in some embodiments, the monitoring device 124 may include sensors to gather patient movement, ambient lighting, and the like. The monitoring device 124 may be physically coupled to the support structure 110 or may be proximate to the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102 and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly as encompassing many individual sensors.

In some embodiments, a communication device 106 may enable the patient 102 to interact with and garnish data from the WCD system 104. The communication device 106 may enable a patient or third party to view patient data, dismiss a shock if the patient is still conscious, turn off an alarm, and otherwise engage with the WCD system 104. In some instances, the communication device 106 may transfer or transmit information, including patient data, to an external device 126, a third-party data server such as a cloud server or a blockchain server. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient, and the WCD system 104 may include a separate communication device 106 remote from the defibrillator 108.

In some embodiments, the communication device 106 may be communicatively coupled to an button 128. The button 128 may be removably coupled to the support structure 110. The patient 102 may couple the button 128 to the support structure 110 or couple the button 128 to an article of clothing. The button 128 may have a wired connection or be wirelessly connected to the communication device 106. In some embodiments, the button 128 may include a visual output, an audio output, and a user input. The visual output may include a light, such as an LED, a small screen, or some combination thereof. Likewise, the audio output may include one or more speakers. The output of the audio output may be loud enough to be heard over nominal background noise. In some embodiments, the audio output might have an adjustable volume range. In some embodiments, the button 128 may include a microphone. In still further embodiments, the button 128 may also include a haptic response.

In some embodiments, the defibrillator 108 may connect with one or more external devices 126. For example, as shown in FIG. 1, the defibrillator 108 may connect to one or more various external devices 126 such as the cloud, a remote desktop, a laptop, a mobile device, a watch, a tablet, a phablet, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include several aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system to make its analysis more accurate since patients' bodies differ from one another. Such parameter values can be stored in a memory of the WCD system and the like. Moreover, a programming interface can be made according to embodiments, which receives such measured values of baseline physiological parameters. Such a programming interface may input automatically in the WCD system these, along with other data.

Figure 2:
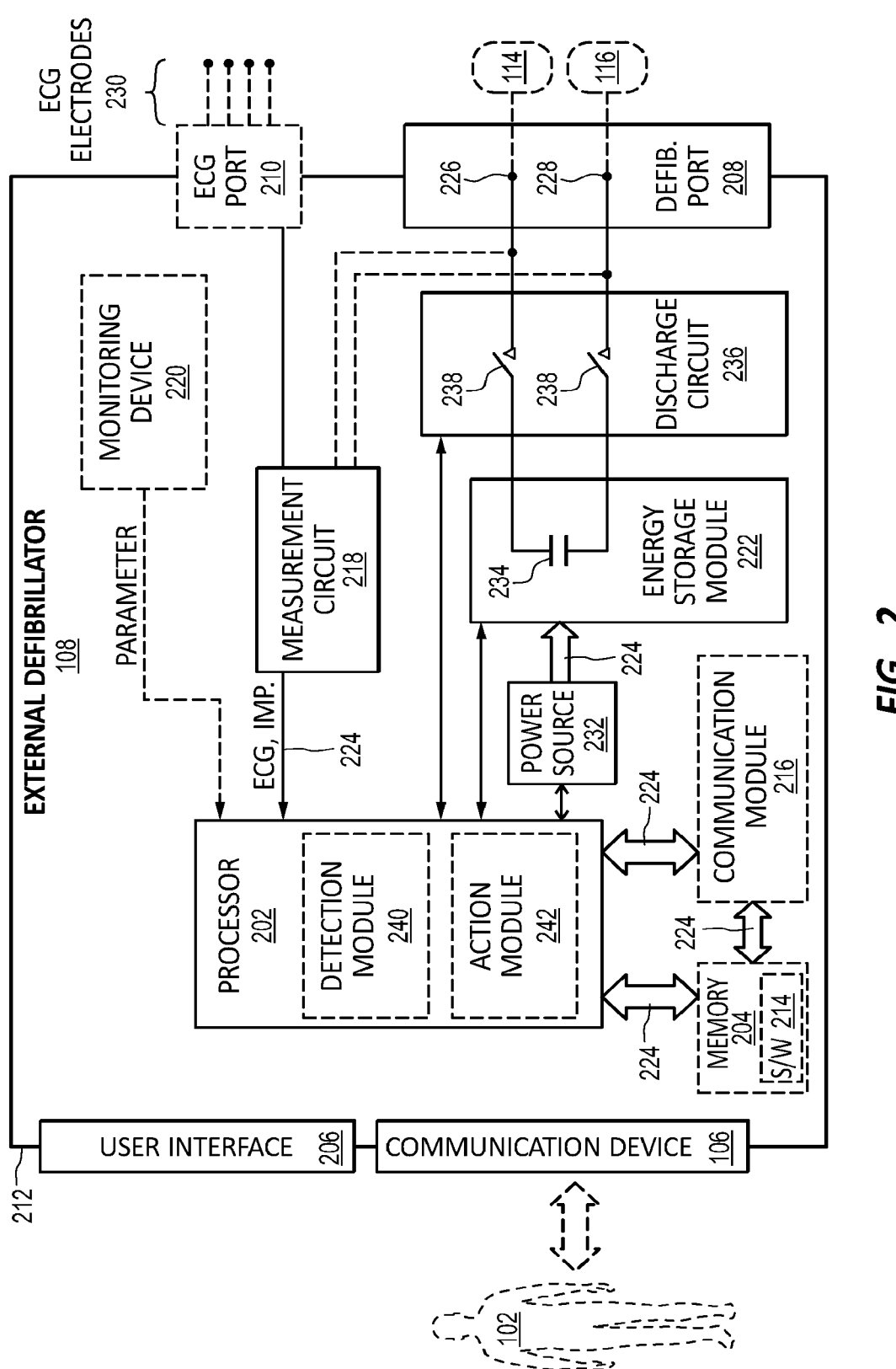
FIG. 2 is a block diagram of an example defibrillator in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read-only memory (ROM), flash RAM, external memory drives, and/or other types. The memory 204 may store computer-readable, computer-executable software/ firmware code 214, including instructions that, when executed, cause the processor 202 to perform various functions (e.g., determine shock criteria, determine heart rate, issue shock command, issue alerts, etc.). In some embodiments, the processor 202 may include an intelligent hardware device, e.g., a central processing unit (CPU), a microcontroller, an application-specific integrated circuit (ASIC), etc.

In some embodiments, the memory 204 can contain, among other things, the Basic Input-Output system (BIOS), which may control basic hardware and/or software operations such as interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 206 may be in addition to or part of the communication device 106. The user interface 206 may display an ECG of the patient, a status of the defibrillator 108, a status of a charge (e.g., a battery charge or an energy storage module), and the like.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g., defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g., leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization, timing, or both. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 220 within the housing 212. The monitoring device 220 may monitor at least one local parameter. Local parameters may include a physical state of the patient such as ECG, movement, heart rate, pulse, temperature, and the like. Local parameters may also include a parameter of the WCD system (e.g., WCD 104, FIG. 1), defibrillator 108, environmental parameters, or the like.

In some embodiments, the WCD system 104 may include an internal monitoring device 220 and an external monitoring device (e.g., external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate to an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy to prepare or anticipate providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrically couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include one or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardwire separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, etc. In some embodiments, the communication module 216 may include a display screen to display messages to the patient. In some embodiments, the display screen may be a touch screen, backlit screen, passive, reflective LCD screen, or the like.

In further embodiments, the communication module 216 may include one or more LEDs which may also convey information to the patient. In some embodiments, the LED brightness may be modulated; the LEDs may be color-changing and the like. In some embodiments, if multiple LEDs are present, each LED may represent various bits of information. For example, one LED may represent heart rate information and enable the patient to quickly determine their heart is operating normally. Another LED may represent the heart rate signal to ensure the patient the heartrate readings are being properly transmitted. Another LED may also represent system status and allow the patient to easily ascertain that the system is fully functioning.

In some embodiments, the processor 202 may execute one or more modules. For example, the processor 202 may execute a detection module 240 and/or an action module 242. The detection module 240 may be a logic device or algorithm to determine if any or a variety of thresholds are exceeded, which may require an action from the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of battery power at the power source 232 or the energy storage module 222, or one or more electrodes (e.g., ECG electrodes, defibrillation electrodes) may have lost connection. In such instances, the action module 242 may trigger an alert to the patient or an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
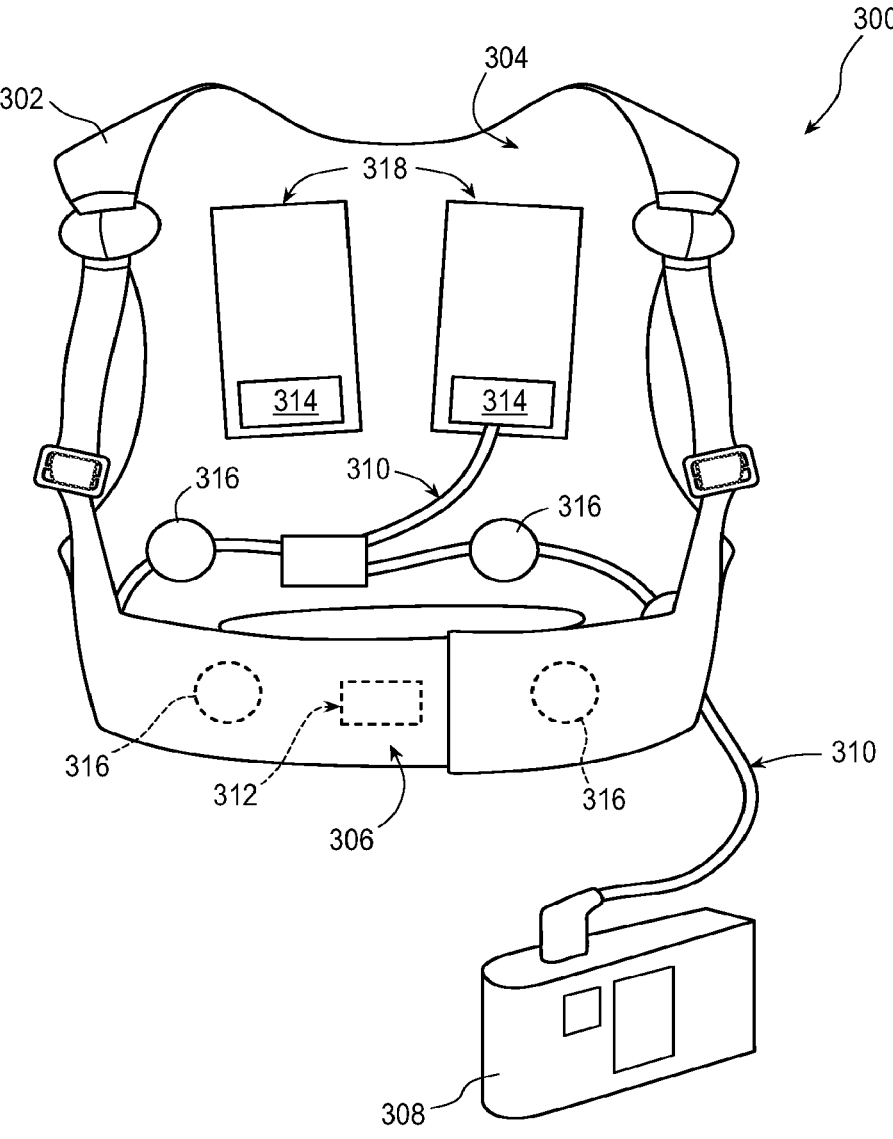
FIG. 3 is a diagram of sample embodiments of components of a WCD system in accordance with exemplary embodiments described herein.

FIG. 3 is a diagram of sample embodiments of components of a WCD system 300 according to exemplary embodiments. The WCD system 300 may be an example of the WCD system 104 described with reference to FIG. 1. In some embodiments, the WCD system 300 may include a support structure 302 comprising a vest-like wearable garment. In some embodiments, the support structure 302 has a backside 304 and a frontside 306 that closes in front of a chest of the patient.

In some embodiments, the WCD system 300 may also include an external defibrillator 308. The external defibrillator 308 may be an example of the defibrillator 108 described with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of the pockets 318 may comprise loose netting so that the electrodes 314 can contact the back of the patient. In some instances, a conductive fluid may be deployed to increase connectivity. Additionally, in some embodiments, sensing electrodes 316 are maintained in positions that surround the patient's torso for sensing ECG signals and/or the impedance of the patient.

In some instances, the ECG signals in a WCD system 300 may comprise too much electrical noise to be useful. To ameliorate the problem, multiple ECG sensing electrodes 316 are provided for presenting many options to the processor (e.g., processor 202, FIG. 2). The multiple ECG sensing electrodes 316 provide different vectors for sensing the ECG signal of the patient.

Figure 4:
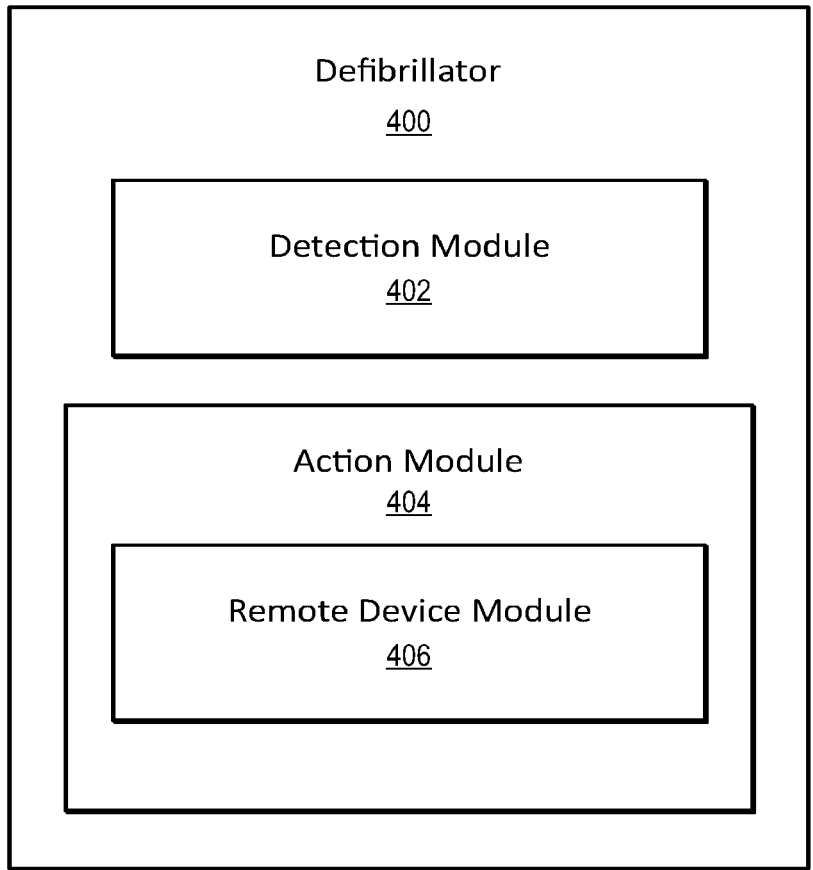
FIG. 4 is a block diagram of an example defibrillator in accordance with exemplary embodiments described herein.

FIG. 4 is a block diagram illustrating components of one example of a defibrillator 400. The defibrillator 400 may be an example of the defibrillator 108 described with reference to FIGS. 1 and 2 and defibrillator 308 described with reference to FIG. 3. In this example, the defibrillator 400 has a detection module 402 and an action module 404. The detection module 402 and action module 404 may be examples of the detection module 240 and the action module 242 described with reference to FIG. 2. In some embodiments, the action module 404 may include a remote device module 406.

The detection module 402 may aid in the detection of various shockable conditions. For example, the detection module 402 may receive a signal from at least one electrode and analyze the signal for a heart rate and other indicators of an abnormal heart condition. If a shockable or monitoring condition exists, the detection module 402 may communicate the need for action to the action module 404.

In some embodiments, the detection module 402 may also detect system conditions. For example, the detection module 402 may determine a battery status of the defibrillator. This may enable the detection module 402 to issue an alert when the battery status is below an acceptable threshold. The detection module 402 may also monitor a status of the electrodes to determine if the electrodes are properly secured to the patient and the leads are all functioning appropriately. The detection module 402 may also track a status of the various other components of the WCD system, such as the button, remote monitoring device, and the like. The detection module 402 may track conditions of the defibrillator itself. For example, the detection module 402 may detect device orientation, movement, external forces, and the like.

In some embodiments, based at least in part on information and data from the detection module 402, the action module 404 may take one or more actions. For example, if a shockable rhythm is detected, the action module 404 may cause a shock to be issued to the patient. In other embodiments, the action module 404 may convey information to the patient. In some embodiments, the action module 404 may include a remote device module 406, which may assist in providing alerts and information to a patient.

For example, the remote device module 406 may in communication with one or more remote devices associated with the patient and the defibrillator 400. The remote device module 406 may push notifications to a remote device in communication with the defibrillator 400. The alarm module 408 may also simultaneously issue the alerts and alarms to the patient via a user interface on the defibrillator 400.

In some embodiments, the remote device module 406 controls the emission of alarms and the basic alarm message content. In some embodiments, the remote device module 406 controls the detailed alarm message content. In alter-native embodiments, the remote device may control the detailed alarm message content.

The remote device module 406 remains independent of the remote device and the action module 404. The action module 404 will still issue alerts to the user and retains control of initiating and presenting the basic alarm message content. The action module 404 communicates these alarms to the remote device module 406, which also pushes the remote device's information.

Figure 5:
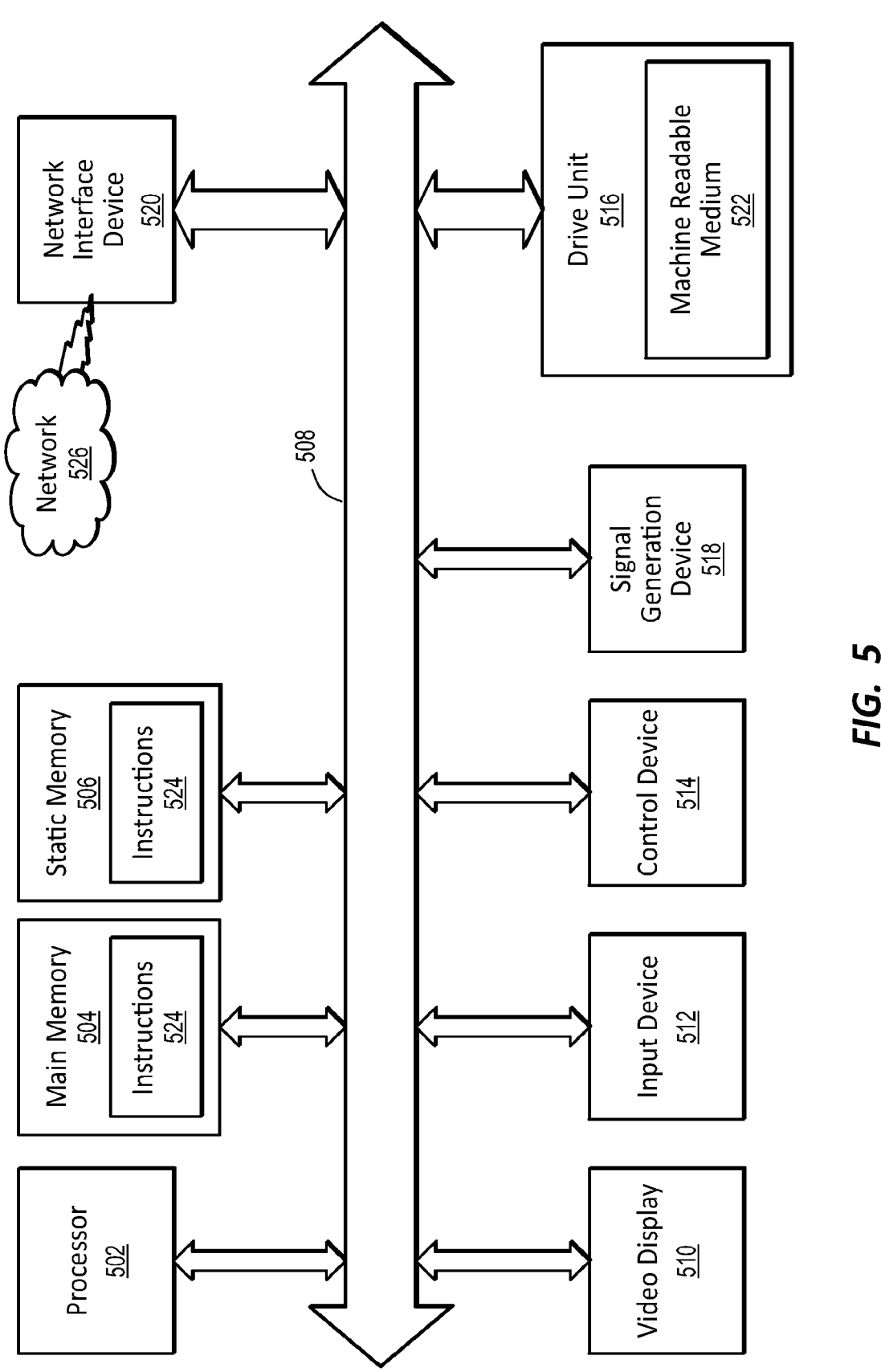
FIG. 5 is a block diagram of an example computer device according to exemplary embodiments described herein.

FIG. 5 is a diagram displaying various components of an example device 500. The device 500 may include a set of instructions causing the device 500 to perform any one or more of the methodologies described herein. In some embodiments, the device 500 may be an example of devices 126 as shown in FIG. 1. In alternative embodiments, the device 500 may operate as a standalone device or may be connected (e.g., networked) to other machines. In a networked deployment, the device 500 may operate in the capacity of a server or a client machine in a server-client network environment or as a peer machine in a peer-to-peer (or distributed) network environment. The device 500 may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single device 500 is illustrated, the term "machine" shall also be taken to include any collection of machines that individually or jointly execute a set (or multiple sets) of instructions to perform any one or more of the methodologies discussed herein.

The device 500 includes a processor 502 (e.g., a central processing unit (CPU), a graphics processing unit (GPU) or both), a main memory 504, and a static memory 506, which communicate with each other via a bus 508. The device 500 may further include a video display unit 510 (e.g., a liquid crystal display (LCD) or a cathode ray tube (CRT)). The device 500 also includes an alphanumeric input device 512 (e.g., a keyboard), a cursor control device 514 (e.g., a mouse), a disk drive unit 516, a signal generation device 518 (e.g., a speaker), and a network interface device 520.

The disk drive unit 516 includes a machine-readable medium 522 on which is stored one or more sets of instructions (e.g., software 524) embodying any one or more of the methodologies or functions described herein. The software 524 may also reside, completely or at least partially, within the main memory 504 and/or within the processor 502 during execution thereof by the device 500, the main memory 504, and the processor 502 also constituting machine-readable media. In alterative embodiments, software 524 may completely or partially reside within the static memory 504.

The software 524 may further be transmitted or received over a network 526 via the network interface device 520.

While the machine-readable medium 522 is shown in an example embodiment to be a single medium, the term "machine-readable medium" should be taken to include a single medium or multiple media (e.g., a centralized or distributed database and/or associated caches and servers) that store the one or more sets of instructions. The term "machine-readable medium" shall also be taken to include any medium that is capable of storing, encoding, or carrying a set of instructions for execution by the machine and that cause the machine to perform any one or more of the methodologies of the present invention. The term "machine-readable medium" shall accordingly be taken to include, but not be limited to, solid-state memories, optical and magnetic media, and carrier wave signals.

Figure 6:
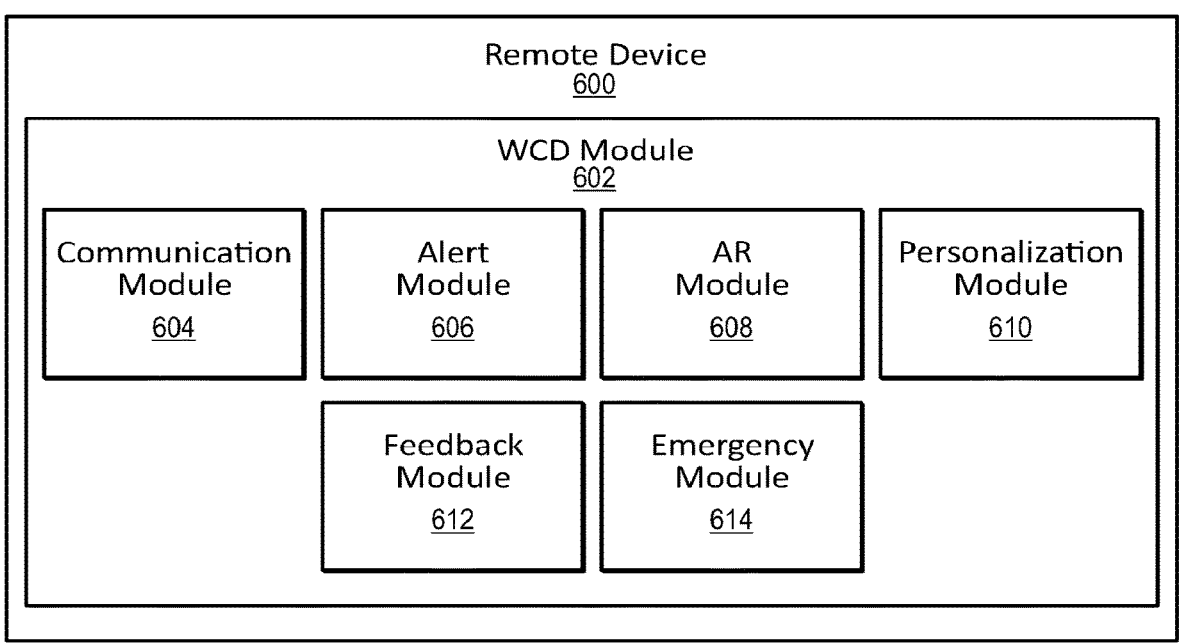
FIG. 6 is a block diagram of an example computer device according to exemplary embodiments described herein.

FIG. 6 is a block diagram illustrating components of one example of a remote device 600. The remote device 600 may be an example of the external device 126 described with reference to FIG. 1 and computer device 500 described with reference to FIG. 5. In this example, the remote device 600 has a WCD module 602.

The WCD module 602 may be in communication with a WCD system. For example, the WCD module 602 may include a communication module 604, which may link the remote device with the WCD system and any other remote devices also in connection with the WCD system. The communication module 604 may communicate via RFID technology, Bluetooth technology, a Wi-Fi network, a wireless network, or another form of communication.

The WCD module 602 may receive messages from the WCD system and deliver alerts to the user. For example, an alert module 606 may receive basic alert information from the WCD and transcribe the information into detailed messages for the patient. For example, the WCD may issue a basic alert such as a bad reading, etc., and then transmit this alert to the remote device 600. The remote device 600 may receive the message, which may trigger a more detailed alert.

The more detailed alert may include troubleshooting steps that may aid the patient in addressing the alert. For example, the alert module 606 may have a series of potential causes that may remedy the bad reading. This may include checking electrode connectivity, checking wire connections, and the like. Each step or item may have additional instructions for the patient. For example, the additional instructions may include how to check electrode connectivity to determine if it is a good connection-then proceeding through a flow chart to correct the connectivity if the patient notices an error. Likewise, the alert module 606 may flow through an additional checklist that provides more detailed videos and instructions on correcting potential issues.

The alert module 606 may enable a patient to discretely interact with the WCD. For example, rather than moving around a cumbersome device, the patient may view their remote device 600, such as a cell phone or smartwatch, easily and unobtrusively. The patient may be able to ascertain from this initial view of the alert if their attention is required. If desired, it may allow a patient to move to a more private setting to troubleshoot or address any potential WCD system issues.

In some embodiments, the WCD module 602 may have an augmented reality (AR) module 608, which may enable the patient to use a remote device to interact with the WCD and troubleshoot potential issues. For example, the WCD module 602 may access one or more cameras proximate to the remote device 600. The patient may use the camera to capture images and/or videos of the patient's WCD system. The AR module 608 may analyze the video to provide directions to the patient. For example, the AR module 608 may analyze the data to determine if a wire is loose, a connection is poor, or some other condition that may be interfering with the functionality of the WCD.

In some embodiments, the WCD module 602 may personalize its interaction with the patient. For example, the personalization module 610 may individualize messages to patients, such as using the patient's name in the alarm message content. The personalization module 610 may also use the patient's location in the alarm message content. For example, the remote device 600 may have GPS or other information, which may provide the personalization module

610 with a location of the patient. The WCD module 602 may use the location information to determine if any devices or other equipment may impede the operation of the WCD system. If such a device or equipment is detected, the personalization module 602, combined with the alert module 606, may issue an alert to notify the patient of the potential interference. If the WCD module 602 receives an alert from the WCD system concerning the operation of the WCD system, the personalization module 610, with the alert module 606, may use the combined information to deduce that the equipment/device may actually be interfering with the operation of the WCD and may indicate to the patient to leave the premise.

The personalization module 610 may also customize the messages and alerts delivered to the patient. For example, the personalization module 610 may prompt the patient to determine which type of messages the patient prefers. For example, the WCD module 602 may deliver audible messages, video messages, 3-dimensional messages, text messages, or some combination thereof. Some patients may have a specific preference. Allowing a patient to choose their preferred delivery method for alerts may put a patient at ease. Learning new technology may be difficult and having the ability to select a specific type of message may lessen the burden of the new technology. For example, a patient that is still learning the system may derive more value from video messaging. A patient with poor eyesight might prefer audible messages to ensure they are correctly interpreting the messages.

The personalization module 610 may also enable a patient to customize how the patient is alerted of the incoming messaging. For example, the personalization module 610 may enable the patient to set a specific haptic response or audible noise. This may ensure the patient understands the alert is specific to the WCD system. In still further embodiments, the patient may personalize the alert based on the importance of the message. For example, a more urgent event, like a potential cardiac event, might have a louder, more attention-seeking sound. In contrast, a lower-level alert that may not require immediate attention may use a less intrusive method of alerting the patient.

In some embodiments, the WCD module 602 may improve alerts and messages over time and may also record comments and observations. For example, a feedback module 612 may easily record patient interaction with the WCD module 602 and provide information to the WCD manufacturer, physicians, and the like. The feedback module 612 may also allow for easy patient feedback. For example, after an alert or a message, the patient may have the ability to rate the quality, effectiveness, and accuracy or some combination thereof of the alert. This may enable the WCD module 602 and/or WCD manufacturer to continuously improve the patient experience. For example, the manufacturer may push updates to the WCD module 602 separately and independent of the operation of the WCD. The WCD would remain independent and fully functioning, but the WCD module 602 on the remote device 600 would be updated. This may improve the patient experience and increase patient compliance In some embodiments, the remote device 600 may issue an emergency protocol when a life-threatening event or other cardiac event is detected. For example, an emergency module 614 may be equipped with an emergency protocol for specific high-level alerts. The emergency protocol may include issuing an immediate message to first responders and emergency personnel outlining the specific of the cardiac event and the location of the patient. The message may include a picture of the patient and any other relevant health information, including allergies, other chronic conditions, patient age, current medications, previous pertinent health history, health insurance information, and the like. The message might include whether a shock was delivered, the time of the shock, the strength of the shock, and heartrates before and after the shock. The message may also include emergency contacts and physician information. In still further embodiments, the emergency module 614 may be able to transmit heart rate information as well. This may include historical information such as typical heart rate patterns of the patient.

In some embodiments, the emergency module 614 may also send messages to emergency contacts set by the patient. The emergency contact message may include information including the type of cardiac event, the location of the patient, which emergency personnel was contacted and responded. In some embodiments, the message might indicate a hospital the patient might be taken to. In still further embodiments, the message might include the number of the responding emergency personnel, which may enable the emergency contact to gather pertinent information such as receiving hospital.

Figure 7:
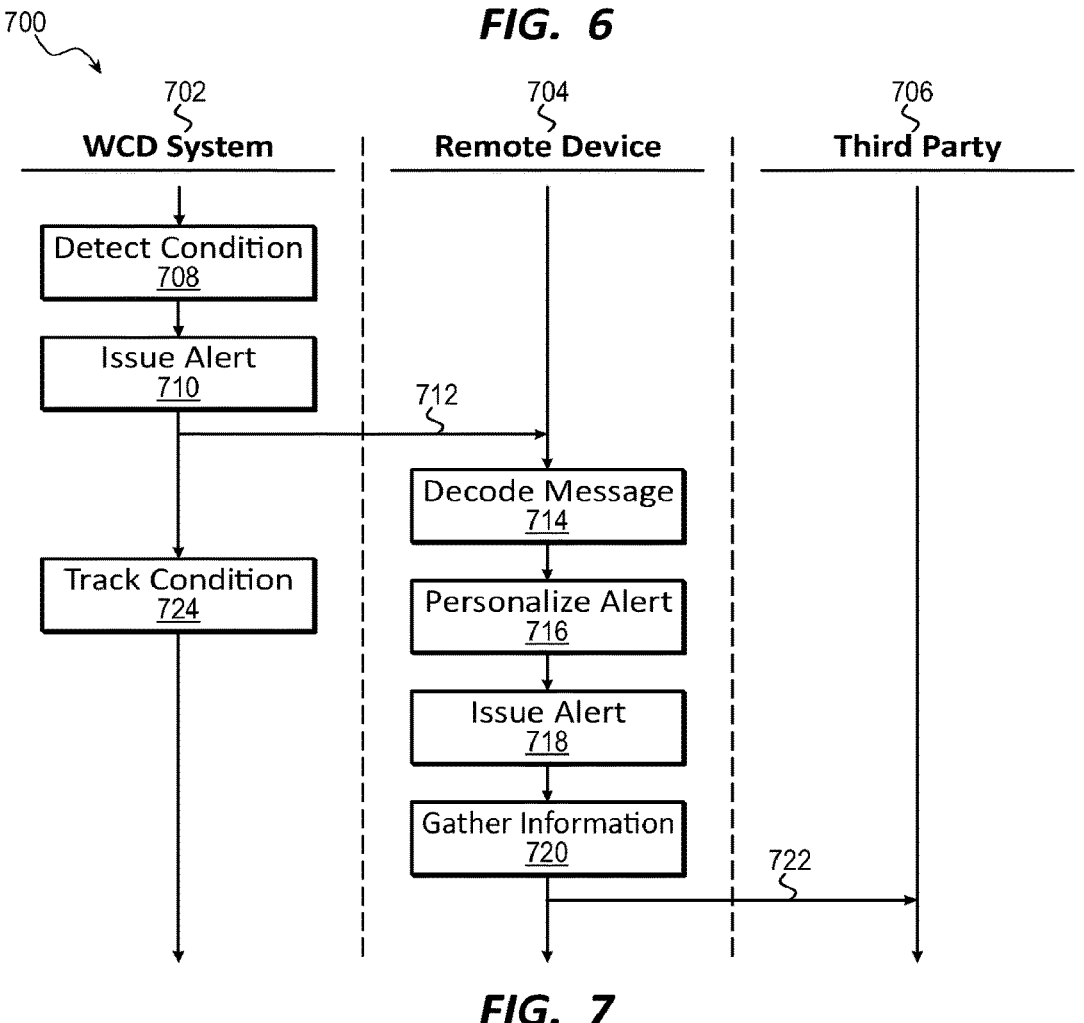
FIG. 7 is a swim lane diagram in accordance with exemplary embodiments described herein.

FIG. 7 is a swim lane diagram of a process 700 for providing alerts and tracking information in a WCD system 702 in communication with at least one remote device 704. In some embodiments, the remote device 704 may also be in communication with a third party 706. The WCD system 702 may be an example of the WCD system 104 or 300 described with reference to FIGS. 1 and 3, respectively. The remote device 704 may be an example of the external or remote devices 126, 500, 600 described with reference to FIGS. 1, 5, and 6. The third party 706 may be an example of a remote server, an emergency contact, emergency services, physicians, WCD manufacturer, emergency personnel, and the like. A system can use the process 700 to generate discrete alerts to a patient, track patient, and WCD information, and transmit that information to a third party 706.

The WCD system 702 may detect a condition 708 that requires an alert. The condition may include a system condition such as a faulty lead, a bad connection, a low battery, or some other system error. The condition may also include a parameter description where the WCD system is detecting a noisy signal or another anomaly that requires troubleshooting. In some embodiments, the condition may be a cardiac condition classified as a cardiac event that may require attention, such as a shock from the WCD system.

Once the condition is detected 708, the WCD system may issue an alert 710. The alert is issued via the WCD system 702. The alert may comprise a series of text alerts, visual alerts, and the like. The WCD system 702 may transmit a coded alert message 712 to a remote device 704. The remote device 704 may receive and decode the message 714. Once the message is decoded, the remote device 704 may personalize the alert 716. As discussed herein, personalization may take on many forms including using the patient's name, preferred alert mode, and preferred messaging mode. In some embodiments, the personalization may also be unique to the type of condition detected.

Once the alert is personalized, the remote device 704 may issue the alert 718. In some embodiments, steps 708 through 718 may continue to cycle for the same condition. For example, if the WCD system 702 detects a condition 708 and issues the alert 710, the WCD system 702 may track the condition 724. If the condition is not resolved within a predetermined time frame set for the particular condition, the WCD system 702 may issue a second alert 710 and continue the process through the remote device 704.

Meanwhile, the remote device 704 may continue to gather and store information 720 from the WCD system as well as feedback from the patient. In some embodiments, the remote device 702 may also collect information independent from the WCD system 702 that may be relevant to the health of the patient. For example, the remote device 702 may gather movement data, location data, weight data, sleep data, nutritional data, and the like. The remote device 720 may then transfer information to a third party 722. The third party 706 may depend in part on the information being transferred. For example, historical heart rate and health information may be transferred to a physician. If a cardiac event requiring a shock or other intervention occurs, the remote device 720 may transfer that information to emergency personnel. The information may include a location of the patient based on GPS data, age, weight, heart history, attending physician, and other relevant details. In still further embodiments, the remote device 720 may additionally or alternatively send information to a patient's emergency contacts. For example, if a patient experiences a cardiac event, in addition to contact emergency personnel, the remote device 720 may send information to the patient's emergency contact. This may include a spouse, significant other, next of kin, child, doctor, or another person as a medical contact for the patient.

Figure 8:
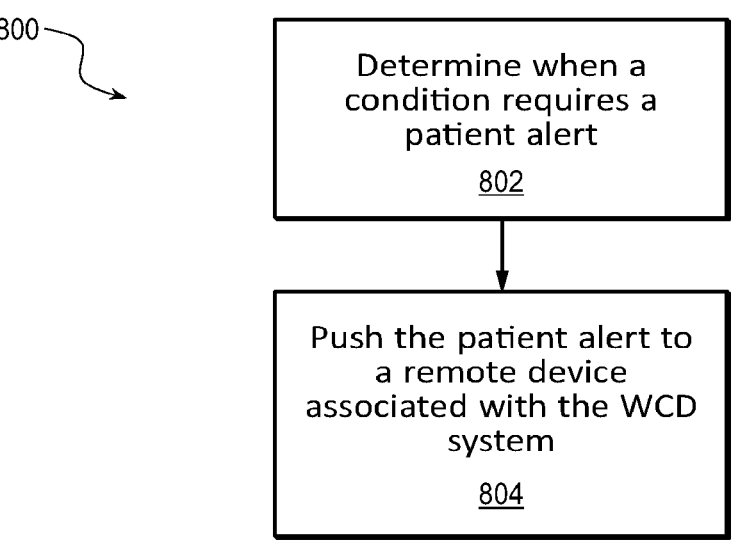
FIG. 8 is a flow diagram in accordance with exemplary embodiments described herein.

FIG. 8 is a flow chart illustrating an example of a method 800 for WCD systems, in accordance with various aspects of the present disclosure. For clarity, the method 800 is described below with reference to aspects of one or more of the systems described herein.

At block 802, the method 800 may determine when a condition requires a patient alert. This may include a cardiac event, an electrode contact issue, or another WCD issue requiring patient attention. At block 804, the method 800 may include pushing the patient alert to a remote device associated with the WCD system 804. In some embodiments, the alert may be a pre-coded message to reduce data storage on the WCD.

Thus, the method 800 may illustrate one method of providing feedback to a user of a WCD system. It should be noted that the method 800 is just one implementation and that the operations of the method 800 may be rearranged or otherwise modified such that other implementations are possible.

Figure 9:
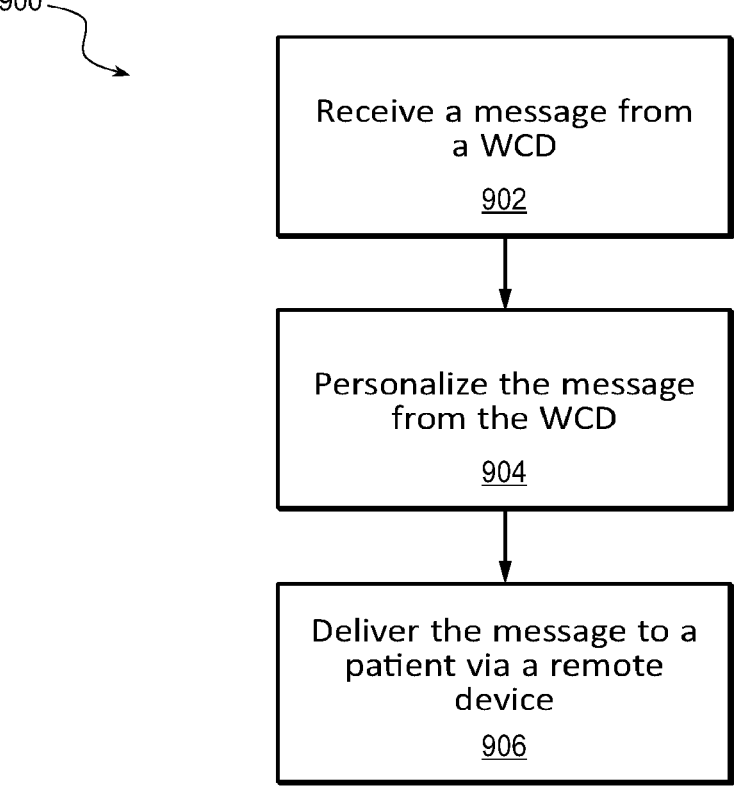
FIG. 9 is a flow diagram in accordance with exemplary embodiments described herein.

FIG. 9 is a flow chart illustrating an example of a method 900 for a device in communication with a WCD system, in accordance with various aspects of the present disclosure. For clarity, the method 900 is described below with reference to aspects of one or more of the systems described herein.

At block 902, the method 900 may receive a message from a WCD. For example, a device may be in communication with the WCD. The WCD may have detected an event requiring patient notification. The WCD may push the notification to the device, which may be received by the device.

At block 904, the method 900 may personalize the message from the WCD. Personalization may take many forms. In some embodiments, the method 900 may add the patient's name to the alert. The method 900 may tailor the alert to the patient's preferences. The patient's preferences may be learned preferences or elected preferences.

At block 906, the method 900 may deliver the message to the patient via the remote device. This may include issuing a notification through the device to the patient. It may come as a pop-up on a home screen, a sound, a musical tone, a vibration, or some other type of indication that the patient has received the message. In some embodiments, the method 900 may deliver a notification or clipped portion of the message to the patient, and the patient may elect to view the message in its entirety.

Thus, the method 900 may provide for one method of providing feedback to a user of a WCD system. It should be noted that the method 900 is just one implementation and that the operations of the method 900 may be rearranged or otherwise modified such that other implementations are possible.

Figure 10:
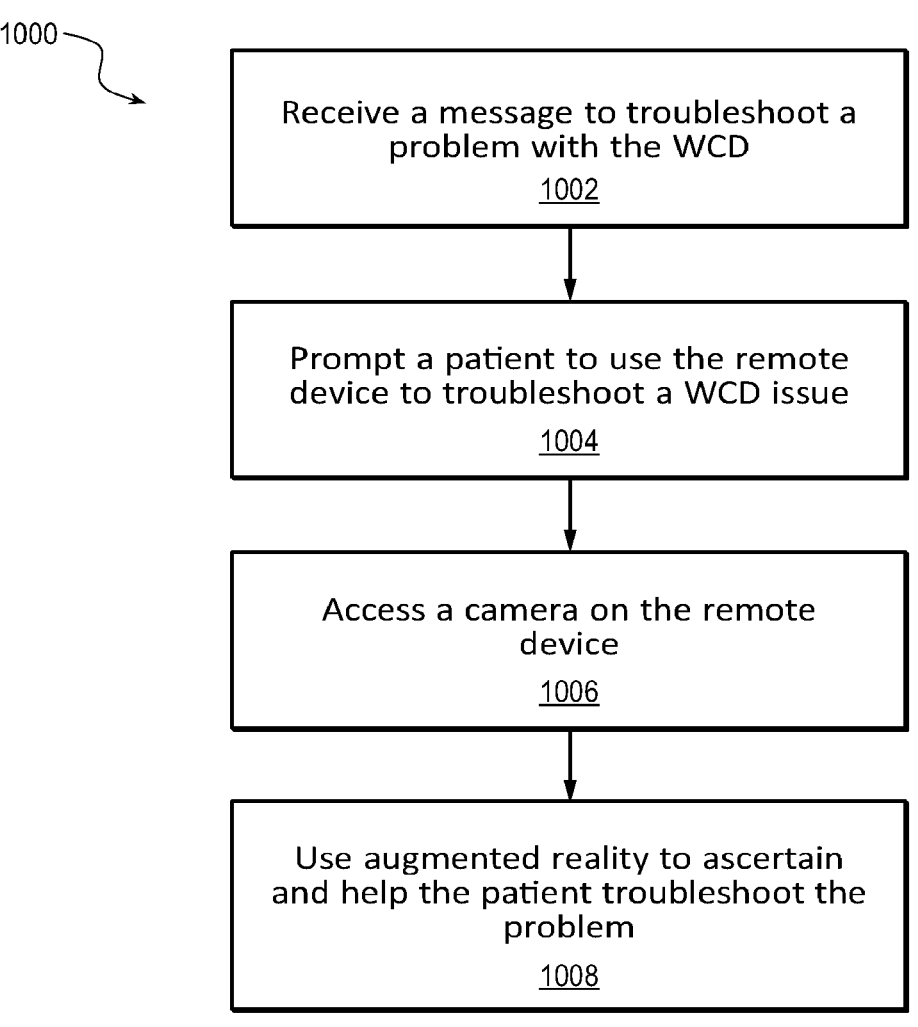
FIG. 10 is a flow diagram in accordance with exemplary embodiments described herein.

FIG. 10 is a flow chart illustrating an example of a method 1000 for a device in communication with a WCD system, in accordance with various aspects of the present disclosure. For clarity, the method 1000 is described below with reference to aspects of one or more of the systems described herein.

At block 1002, the method 1000 may receive a message to troubleshoot a problem with the WCD. The problem may be an electrode connectivity issue, a wiring issue, a battery issue, a positioning issue, and the like. The message may include detailed steps which may walk the patient through the particular issue at hand. The detailed steps may include images or videos to help the patient navigate through the various components of the WCD.

For example, at block 1004, the method 1000 may prompt the patient to use the remote device to troubleshoot the WCD issue. This may include, in some embodiments, prompting the patient to use the device's camera to capture images which may then be analyzed to help the patient navigate the WCD technology. This may result in, at block 1006, the method 1000 accessing a camera on the remote device. In some embodiments, the method 1000 may prompt the patient for permission to use the camera.

At block 1008, the method 1000 may use augmented reality or some similar technology to ascertain and help the patient troubleshoot the problem. This may enable the patient to more easily navigate the technology by being able to view the WCD and determine what may be causing an alert.

Thus, the method 1000 may provide for one method of providing feedback to a user of a WCD system. It should be noted that the method 1000 is just one implementation and that the operations of the method 1000 may be rearranged or otherwise modified such that other implementations are possible.

Figure 11:
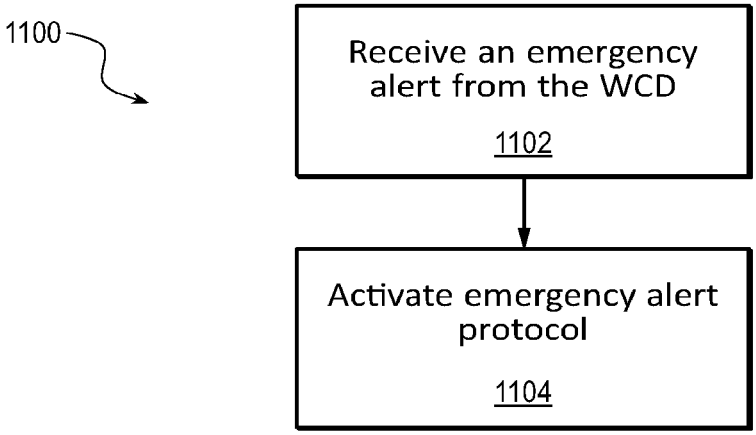
FIG. 11 is a flow diagram in accordance with exemplary embodiments described herein.

FIG. 11 is a flow chart illustrating an example of a method 1100 for a device in communication with a WCD system, in accordance with various aspects of the present disclosure. For clarity, the method 1100 is described below with reference to aspects of one or more of the systems described herein.

At block 1102, the method 1100 may receive an emergency alert from the WCD system. At block 1104, the method 1100 may activate the emergency alert protocol. This may include several different steps and actions based at least in part on the patient and the cardiac event type. The method 1100 may contact emergency personnel with the patient's status and location as well as pertinent health history and information. The method 1100 may additionally or alternatively contact the patient's emergency contact. This may enable the emergency contact to know that an event took place and then take steps to be supportive of the patient.

Thus, the method 1100 may provide for one method of providing feedback to a user of a WCD system. It should be noted that the method 1100 is just one implementation and that the operations of the method 1100 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described in order to prevent unnecessarily obscure this description.

Some technologies or techniques described in this document may be known. Even then, however, it is not known to apply such technologies or techniques as described in this document or for the purposes described in this document.

This description includes one or more examples, but this fact does not limit how the invention may be practiced. Indeed, examples, instances, versions, or embodiments of the invention may be practiced according to what is described, or yet differently, and also in conjunction with other present or future technologies. Other such embodiments include combinations and sub-combinations of features described herein, including, for example, embodiments that are equivalent to the following: providing or applying a feature in a different order than in a described embodiment; extracting an individual feature from one embodiment and inserting such feature into another embodiment; removing one or more features from an embodiment, or both removing a feature from an embodiment and adding a feature extracted from another embodiment while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to," "adapted to," and/or "configured to" denote one or more actual states of construction, adaptation, and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description, a single reference numeral may be used consistently to denote a single item, aspect, component, or process. Moreover, a further effort may have been made in the preparation of this description to use similar though not identical reference numerals to denote other versions or embodiments of an item, aspect, component, or process that are identical or at least similar or related. Where made, such a further effort was not required but was nevertheless made gratuitously so as to accelerate comprehension by the reader. Even where made in this document, such a further effort might not have been made completely consistently for all of the versions or embodiments that are made possible by this description. Accordingly, the description controls defining an item, aspect, component, or process rather than its reference numeral. Any similarity in reference numerals may be used to infer a similarity in the text, but not to confuse aspects where the text or other context indicates otherwise.

The claims of this document define certain combinations and subcombinations of elements, features, and acts or operations, which are regarded as novel and non-obvious. The claims also include elements, features, and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method to alert a user of a wearable cardioverter defibrillator (WCD), the method comprising:

sensing, by the WCD, a cardiac health condition of the user of the WCD;

determining whether the sensed cardiac health condition requires a user alert, the user alert based, at least in part, on the sensed cardiac health condition of the user; and responsive to a determined user alert, pushing the determined user alert to a remote device, the remote device being communicatively coupled with the WCD and configured to personalize the pushed determined user alert via an application interface on the remote device and output the personalized determined user alert to the user, the personalization being customized by the user, wherein the personalization of the determined user alert is based on location information associated with the user, the location information being used to determine whether a device proximate to the user is interfering with operation of the WCD.

2. The method of claim 1, further comprising:

pushing user health data and the location information to the remote device.

3. The method of claim 2, wherein the user health data includes at least one of an age, weight, cardiac history, location of the user, or a combination between the age, the weight and the cardiac history.

4. The method of claim 1, further comprising:

determining whether the sensed cardiac health condition requires intervention; and pushing an alert to the remote device responsive to determining that the sensed cardiac health condition requires intervention, the pushed alert having details of the required intervention.

5. The method of claim 1, further comprising:

detecting a cardiac event requiring intervention; and pushing an alert to the remote device to activate an emergency protocol responsive to detecting the cardiac event requiring intervention.

6. The method of claim 1, wherein to personalize the pushed determined user alert, a specific haptic response or audible alerts are set based on a type of the cardiac health condition of the user.

7. The method of claim 1, wherein pushing the determined user alert to the remote device further comprises activating an emergency protocol upon sensing a type of cardiac health condition, and wherein activating the emergency protocol comprises issuing a message to emergency personnel, the message including information about the cardiac health condition and the location information of the user.

8. A method of alerting a user of a wearable cardioverter defibrillator (WCD), the method comprising:

receiving an alert, from the WCD, on a remote device associated with the user, the remote device being communicatively coupled with the WCD, wherein the alert is based, at least in part, on a sensed health condition of the user;

transcribing, by the remote device, the received alert into a message for the user;

personalizing, by the remote device, the message for the user, the personalizing being responsive to personalization information received via an application interface on the remote device and a learned interaction behavior of the user, the personalizing being customized by the user, wherein the personalizing is based on multimedia data captured by the remote device during troubleshooting by accessing a camera on the remote device to troubleshoot a problem with the WCD and based on location information associated with the user, the location information being used to determine whether a device proximate to the user is interfering with operation of the WCD; and delivering, by the remote device, the personalized message to the user.

9. The method of claim 8, wherein the personalized message includes two or more of an audio message, a voice message, or a video message.

10. The method of claim 8, wherein delivering the personalized message to the user includes:

delivering a message alert with a personalized message presentation based, at least in part, on preferences selected by the user.

11. The method of claim 8, further comprising:

receiving an alert to troubleshoot the problem with the WCD;

prompting the user to use the remote device to troubleshoot the problem with the WCD;

requesting permission to access the camera on the remote device; and using the camera to troubleshoot the problem with the WCD in response to the requested permission being granted.

12. The method of claim 8, further comprising:

receiving an emergency alert from the WCD; and activating an emergency alert protocol.

13. The method of claim 12, further comprising:

determining the location information of the user; and transmitting the location information of the user to emergency personnel.

14. The method of claim 13, further comprising:
transmitting user data to the emergency personnel.

15. The method of claim 13, further comprising:
contacting an emergency contact based on the emergency alert protocol.

16. The method of claim 13, further comprising:
contacting an attending physician of the user; and
delivering the emergency alert to the attending physician.

17. The method of claim 8, further comprising:
storing the alert from the WCD in a memory of the remote device.

18. A method of alerting a user of a wearable cardioverter defibrillator (WCD), the method comprising:
receiving an alert, from the WCD, on a remote device associated with the user, wherein the alert is associated with an alarm outputted or being output by the WCD and based, at least in part, on a sensed cardiac health condition of the user by the WCD;
transcribing the received alert into a message for the remote device;
personalizing the message using personalization information received via an application interface on the remote device, the personalizing being customized by the user, wherein the personalizing is based on multimedia data captured by the remote device during troubleshooting by accessing a camera on the remote device to troubleshoot a problem with the WCD and based on location information associated with the user, the location information being used to determine whether a device proximate to the user is interfering with operation of the WCD;
delivering the personalized message to the user by the remote device; and
storing the alert from the WCD in a memory of the remote device.

19. The method of claim 18, wherein the personalizing is further based on one or more of: a learned interaction behavior of the user of the WCD or a user customization of an interaction with the alert.

20. The method of claim 18, wherein delivering the personalized message to the user includes:
delivering the personalized message based, at least in part, on preferences selected by the user.

* * * * *